United States Patent
Sarkar et al.

(10) Patent No.: US 10,799,154 B2
(45) Date of Patent: Oct. 13, 2020

(54) WALKING AID AND SYSTEM AND METHOD OF GAIT MONITORING

(71) Applicant: Vanderbilt University, Nashville, TN (US)

(72) Inventors: Nilanjan Sarkar, Brentwood, TN (US); Thomas J. Withrow, Brentwood, TN (US); Joshua W. Wade, Murfreesboro, TN (US); Robert Boyles, Nashville, TN (US); Alec Myszka, Nashville, TN (US); Esube T. Bekele, Nashville, TN (US); Marco Beccani, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/068,317

(22) Filed: Mar. 11, 2016

(65) Prior Publication Data
US 2016/0262661 A1   Sep. 15, 2016

Related U.S. Application Data

(60) Provisional application No. 62/131,461, filed on Mar. 11, 2015.

(51) Int. Cl.
*A61B 5/11* (2006.01)
*A45B 3/00* (2006.01)
(Continued)

(52) U.S. Cl.
CPC .............. *A61B 5/112* (2013.01); *A45B 3/00* (2013.01); *A61B 5/6887* (2013.01); *G01L 5/00* (2013.01);
(Continued)

(58) Field of Classification Search
CPC ....... A61B 5/103; A61B 5/112; A61B 5/6887; A61H 3/00; A61H 3/002; A61H 3/04;
(Continued)

(56) References Cited

U.S. PATENT DOCUMENTS 4,280,204 A   7/1981 Elchinger
5,226,718 A * 7/1993 Lin .......................... A45B 3/04
                                                    362/102

(Continued)

OTHER PUBLICATIONS

Internet Archive, Sensitronics Webiste "1 Inch ShuntMode FSR", Jun. 15, 2014. Retrieved from <https://web.archive.org/web/20140615151203/https://sensitronics.com/products-1-inch-shunt-mode-fsr.php> on Apr. 17, 2018.*

(Continued)

*Primary Examiner* — David J. McCrosky
(74) *Attorney, Agent, or Firm* — Michael Best & Friedrich LLP

(57) ABSTRACT

A clinical assessment tool coupled to a walking aid for enhancing a therapist's observation-based gait assessment with use of additional objective and quantitative data such as acceleration, angular velocity, and applied forces. The assessment tool facilitates appropriate assistive gait device prescription, provides patients and therapists feedback during gait training, and reduces wrist and shoulder injuries with walking aid usage. The assessment tool is configured to detect timing and speed of walking aid, placement, angular acceleration of the walking aid, and amounts of weight borne on the walking aid.

12 Claims, 12 Drawing Sheets

(51) Int. Cl.
*A61B 5/00* (2006.01)
*G01L 5/00* (2006.01)
*G01P 15/00* (2006.01)
*G01P 3/00* (2006.01)

(52) U.S. Cl.
CPC .............. *G01L 5/0004* (2013.01); *G01P 3/00* (2013.01); *G01P 15/00* (2013.01)

(58) Field of Classification Search
CPC ................ A61H 3/06–068; A61H 3/02; A61H 2201/5058; A61H 2201/5061; A61H 2201/5084; A45B 3/00; A45B 3/008; A45B 9/02; A45B 2009/002; A45B 9/04; A45B 2009/005; A45B 2009/007; A45B 3/08; A61G 2203/32–38; A61G 2203/42; A61G 2203/44; A61G 2203/30–38
USPC ................................................. 600/587, 595
See application file for complete search history.

(56) References Cited

U.S. PATENT DOCUMENTS

| | | | | |
|---|---|---|---|---|
| 5,511,571 | A * | 4/1996 | Adrezin | A61B 5/1038 135/66 |
| 6,469,956 | B1 | 10/2002 | Zeng | |
| 7,826,983 | B2 * | 11/2010 | Alwan | A61B 5/1038 702/33 |
| 8,082,936 | B2 | 12/2011 | Goldberg et al. | |
| 8,393,342 | B2 | 3/2013 | Goldberg et al. | |
| 8,418,705 | B2 * | 4/2013 | Ota | A61H 3/04 135/71 |
| 8,467,674 | B1 * | 6/2013 | Ratner | F16M 11/28 396/310 |
| 8,538,722 | B2 * | 9/2013 | Naya | G06K 9/00335 600/595 |
| 8,974,232 | B2 | 3/2015 | Behrenbruch et al. | |
| 9,513,126 | B2 * | 12/2016 | Sun | G01C 21/005 |
| 2014/0276242 | A1 * | 9/2014 | Chen | A61B 5/112 600/595 |
| 2015/0282766 | A1 * | 10/2015 | Cole | A61B 5/7267 702/139 |
| 2016/0253890 | A1 * | 9/2016 | Rabinowitz | A61H 1/02 |
| 2017/0224573 | A1 * | 8/2017 | Challa | A61H 3/0288 |

OTHER PUBLICATIONS

Henry, et al. "Gait monitoring for the elderly using a robotic walking aid." Electrical and Electronics Engineers in Israel (IEEEI), 2010 IEEE 26th Convention of. IEEE, 2010. (Year: 2010).*
Yusro, M., et al. "SEES: Concept and design of a smart environment explorer stick." Human System Interaction (HSI), 2013 the 6th International Conference on. IEEE, 2013. (Year: 2013).*
Machine Translation of CN105788489 (Year: 2016).*
Engineering Design Handbook—Maintainability Guide for Design: (AMCP 706-134). U.S. Army Materiel Command. Chapter 23. Oct. 1972. Retrieved from https://app.knovel.com/hotlink/toc/id:kpEDHMGDA1/engineering-design-handbook-24/engineering-design-handbook-24 (Year: 1972).*
Pirttikangas, S. et al. "Feature selection and activity recognition from wearable sensors." International symposium on ubiquitious computing systems. Springer, Berlin, Heidelberg, 2006. (Year: 2006).*
Wu, Winston et al., "The SmartCane System: An Assistive Device for Geriatrics," BodyNets (2008).
Lan, Mars et al., "SmartFall: An Automatic Fall Detection System Based on Subsequence Matching for the SmartCane," BodyNets (2009).
Culmer, Peter et al., "An Instrumented Walking Aid to Assess and Retrain Gait," IEEE/ASME: Transactions on Mechatronics vol. 19, No. 1 (Nov. 16, 2012).
Vaibhav, Singh et al., "'Smart' Cane for the Visually Impaired: Design and Controlled Field Testing of an Affordable Obstacle Detection System."
Furlan, Cornelio and Su, Vivian, "Sonar Walking Stick" (2014).
Cardin, Sylvain et al., "Wearable Obstacle Detection System for Visually Impaired People," VR Workshop on Haptic and Tactile Perception of Deformable Objects (2005).
Sound Foresight Technology Limited, ". . . putting the world at your fingertips Introducing the all new UltraCane . . . " https://www.ultracane.com/.
NevonProjects, "Ultrasonic Blind Walking Stick," http://nevonprojects.com/ultrasonic-blind-walking-stick-project/.
Russon, Mary-Ann, "SmartCane: A Smart WAlking Stick That Uses Sonar to Guide Blind People," International Business Times (Jun. 20, 2014).
Senthilingam, Meera, "Sonar sticks use ultrasound to guide blind people," CNN (Jul. 15, 2014).

* cited by examiner

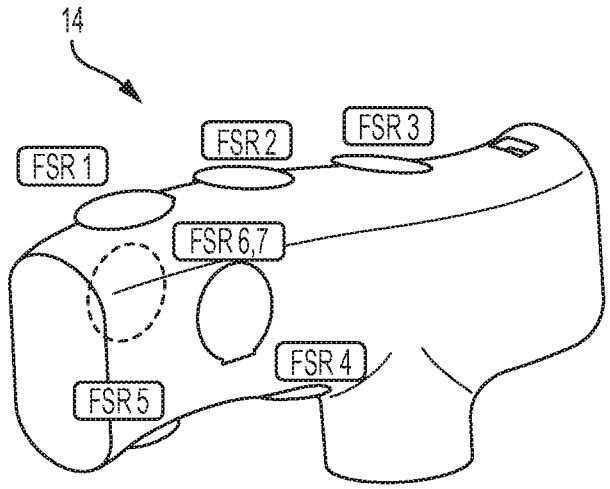
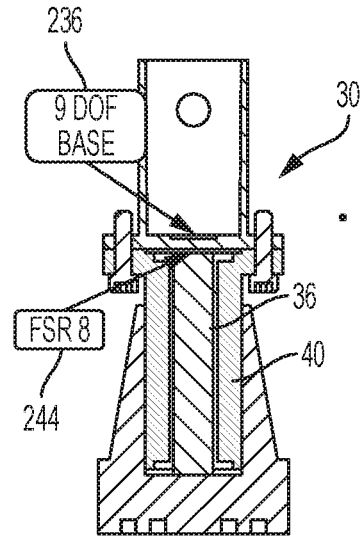
FIG. 9A
FIG. 9B
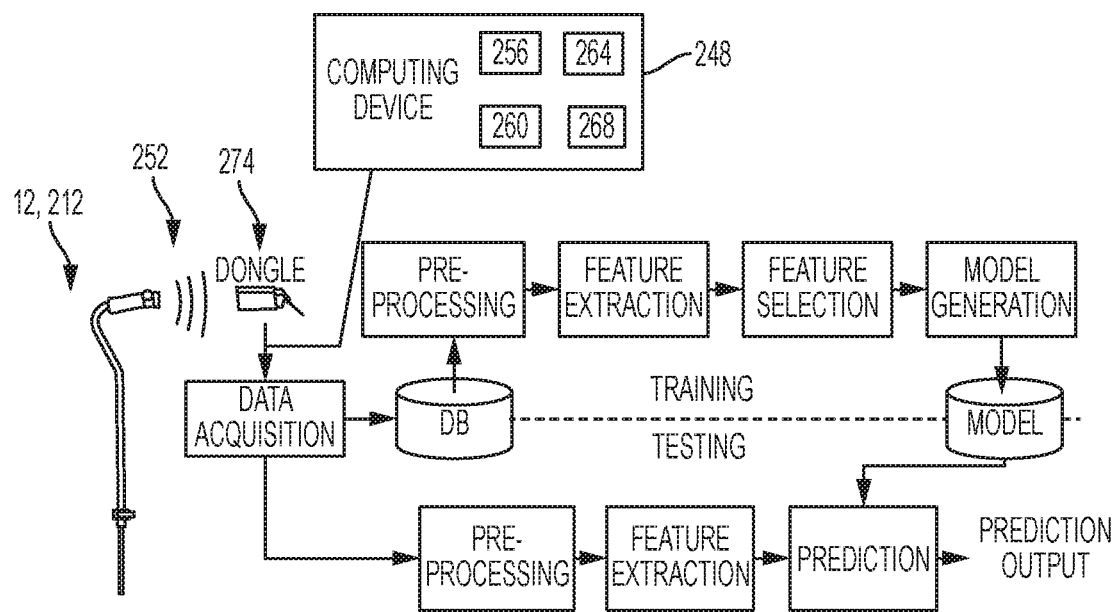
FIG. 10

WALKING AID AND SYSTEM AND METHOD OF GAIT MONITORING

CROSS-REFERENCE TO RELATED APPLICATIONS

This application is a non-provisional application of and claims priority to U.S. Provisional Patent Application No. 62/131,461, filed on Mar. 11, 2015, the contents of which are incorporated herein by reference.

BACKGROUND OF THE INVENTION

Independent and safe mobility is an important goal in an individual's life. To achieve this, however, an assistive device such as a cane or a walker may need to be used after a fall, injury, or functional decline. As people are living longer, the use of mobility aids has been steadily increasing. In the last 15 years alone, the number of people in the United States relying on mobility aids to achieve independent mobility has increased from 4.4 to 8.5 million. Among mobility aids, the cane is the most commonly used device by adults aged 65 to 89. Primary reasons for increased use of mobility aids are imbalance and falls, seen increasingly with advanced age. Falls among the 65 and over population are increasingly common. One out of three adults from this group experiences a fall annually, which can lead to hip and other fractures, traumatic brain injury, or even death—all with an enormous annual medical cost of $34 billion.

Mobility-trained physical therapists (PT) analyze gait, assess fall risk, and make skilled recommendations pertaining to walking aid selection and usage. Common functional balance measures currently used to quantify a patient's risk of fall include evidence-based indices such as the Dynamic Gait Index (DGI), Functional Gait Assessment (FGA), and the Berg Balance Test (BBT). While these measures have demonstrated validity and reliability in the qualitative examination of functional mobility and fall risk, we believe that there are ways to make such evaluation mechanisms even stronger. Existing methods do not provide quantitative data to characterize mobility device usage, for example, how much weight is being borne on the cane, how a person is moving the cane, and if there are changes in patterns of usage over time. Typical physical therapy gait and balance evaluations are limited to 30 to 60 minutes within current clinical settings. Potentially beneficial information regarding the use of a mobility aid over long periods of time and in naturalistic settings would not only provide a more accurate picture of a person's mobility, but would also provide data to identify finer positive or negative changes in mobility over time, leading to potentially early identification of changes in functional status. With the current invention, data collected from outside the clinic can be used to more fully inform the PT's diagnosis and progress-monitoring, which is currently not possible using existing methods.

While long-term computer-assisted monitoring of patient mobility by health care providers has not yet made its way into medical practice, it is a burgeoning area of research. Several groups have recently begun investigating the monitoring of patient performance by instrumenting shoes, walking canes, and walkers with sensors to gain a deeper, more objective understanding of patient mobility. Glover et al. (2004) put a GPS on a walker in order to create predictive models of users' behavior based on time of day, device location, and the user's movements. They achieved a high level of prediction accuracy in predicting user activities such as going to lunch. While this type of system was shown to be robust, it does not address the same issues that we are trying to address with the present invention, namely detection of finer grained user activities and evaluation of fall likelihood through correlating sensor data patterns with PTs' evidence-based evaluations.

Lan et al. (2009) created the real-time fall detection algorithm SmarfFall for their SmartCane system, which consisted of a wireless electronics module that collected inertial and load data from a modified cane. The SmartFall algorithm was designed to detect a fall incident on the fly based on a three-stage pattern of a likely fall: collapse and then impact followed by inactivity. They showed that this algorithm was strong at detecting simulated falls. Note that, importantly, this algorithm does not predict fall risk. A major weakness of fall-detection in general is that there is simply not enough publicly available data with which to train a robust fall prediction model. Falls are unanticipated events, and what little real-world fall data that does exist has been collected largely via body sensors rather than from mobility aids. Moreover, Klenk et al. (2011) showed that there is little correlation between simulated falls and real-world falls data, suggesting that models trained on healthy young people are likely not generalizable to the at-risk population. Work on the SmartCane system has recently evolved into a business partnership with the company Isowalk, Inc., and reportedly offers cloud-based analysis of device data; at the time of this writing, no new publications have appeared regarding the system. While both the present invention and the Isowalk system propose analysis of mobility device usage data for patient benefit, only the present invention aims to apply machine learning techniques for the purposes of both user activity and functional ability prediction. Recently, Lemoyne et al. (2015) mounted an iPod onto a cane and collected acceleration data from the device's built-in accelerometer in order to predict "appropriate" or "inappropriate" cane usage. Using logistic regression to predict user activity, they were able to demonstrate a high degree of prediction accuracy.

Culmer et al. (2014) developed the iWA, or instrumented Walking Aid. Like the SmartCane, the iWA augments a standard cane with a wireless module that collects data from load and accelerations. Data from the iWA is intended to be used to analyze load and device orientation at a high degree of accuracy. Culmer et al. offer the system as not only an objective tool for accurately measuring load and speed, but also as an alternative to kinematic monitoring systems that rely on markers and cameras to track pose. While this device usage information would certainly be useful to a PT, the iWA does not provide information about home compliance, fall risk, user activity, or functional decline. In contrast to instrumented mobility aids, other kinds of computer-based systems have been adopted by PTs and have been shown to be effective tools. The Balance Master, for instance, uses a moving platform to test the balance-shifting ability of the subject standing on it. The Balance Master system was shown to measure balance data that correlated well with an observation-based evaluation test, which further strengthens our argument that objective data measures may be correlated with current best practices. Another example of technology being used to complement evaluation indices is that of the GAITRite walkway system. A subject walks along the GAITRite mat and the system reports data related to foot placement, weight-shifting, and velocity.

SUMMARY OF THE INVENTION

Embodiments of the invention provide a clinical assessment tool centered on a standard walking cane embedded system that can enhance a therapist's observation-based gait assessment with use of additional objective and quantitative data such as acceleration, rotational velocity, and force application. In particular, this system can be utilized to detect timing and speed of cane placement, angular acceleration of the cane, and amounts of weight borne on the cane. This system includes a hardware and software platform and is designed to assist physical therapists in collection of objective data during gait analysis, to facilitate appropriate assistive gait device prescription, to provide patients and therapists feedback during gait training, and to reduce wrist and shoulder injuries with cane usage.

Embodiments of the invention provide a device that demonstrates modularity that allows various base ferrule alternatives as well as disconnection of the base module without disturbing the rest of the system. A custom, low power, highly modular microelectronics system was developed and embedded within the manufactured housings to wirelessly stream data to a PC application for data logging and analysis. This system was shown to reliably predict a user's activity using information from force and inertial information collected from the device's sensors. This device also has the capacity to be used outside the clinical setting in order to obtain long term analysis of a person's gait. The system responds to the need from therapists for quantitative, objective measurement of an individual's gait patterns and paves the way for further development and validation of such a system.

Embodiments of the system may be used to recognize falls and near-falls through the same techniques that allow the current system to distinguish walking from stair-climbing. This kind of information will be important to an individual's healthcare providers and may ultimately prove to be lifesaving.

In one embodiment, the invention provides an instrumented cane embedded system that can precisely monitor gait behavior with the goals of (1) reinforcing clinical evaluations with objective information and (2) detecting gait anomalies such as falls, stumbles or similar events as well as early indications of gait patterns that may predict illnesses like Parkinson's disease. Such a system can help the therapist to enhance his/her assessment in order to make objective and standardized evaluations of individuals.

A therapist may interact with the system through a graphical user interface (GUI), either in real-time or offline, to monitor and analyze data associated with a patient. In a real-time data monitoring scenario, the GUI may be used by the therapist to observe quantities related to weight-bearing, acceleration, and grip intensity collected from the cane while the patient is using it. FIG. 13 shows a screenshot of a real-time data monitoring session in which sensor data is displayed alongside other useful metadata, such as patient identification, gait task type, and packet loss information. This GUI may also be used offline to "replay" (i.e., review) session data. Another instance of the GUI is designed specifically for use in logging objective data during clinical assessments and is shown in FIG. 14. This GUI provides easy-to-use tools for logging objective data based on task type (e.g., FGA or DGI) and patient fall risk, and displays metadata related to the clinical session such as dongle connection status, received packet count, and logged packet count. FIG. 15 shows a conceptual rendering of a more sophisticated GUI in which the therapist is able to isolate data from a specific session, plot the signals, compute descriptive statistics over segments of the signal window, and perform predictive analytics on the signal window using our machine learning prediction methods; although this is a conceptual GUI, these functionalities currently exist in a command-line application. Predictions on these signal windows can be configured to report activity predictions (e.g., walking, standing, stairs ascent/descent), and, as more patient data is collected and included in the prediction model, types of mobility-impairments (e.g., injury, visual impairment, Parkinson's disease, etc.). PDF reports may be generated from session data and filed by therapists alongside current assessment documents like the FGA or DGI. These reports may contain descriptive statistics of various signals of interest (e.g., mean, standard deviation, skewness), as well as tables containing activity prediction rates by activity type.

In one embodiment, the invention provides an instrumented cane including a power source, at least two types of sensors, and a controller for transmitting data to a peripheral device.

In another embodiment the invention provides a system for predicting a state of action of a user of an instrumented cane, where the system includes a data acquisition module, a feature extraction module, a feature selection module, a model generation module, and a prediction module.

In yet another embodiment, the invention provides a gait monitoring device comprising a walking aid, a plurality of first sensors disposed on the walking aid, the first sensors configured to detect a first force. The device also comprises a second sensor coupled to the walking aid and configured to detect an acceleration value and an angular velocity value and a third sensor coupled to the walking aid and configured to detect a second force. The device also comprises a microcontroller in electrical communication with the first sensors, the second sensor, and the third sensor, the microcontroller configured to electronically transmit the first force from the first sensor, the acceleration value and angular velocity value from the second sensor, and the second force from the third sensor to a peripheral device for electronic processing and outputting information related to a gait pattern of a patient.

In another embodiment, the invention provides a diagnostic device comprising a plurality of first sensors coupleable to a walking aid, the first sensors configured to detect a first force applied to the walking aid; a second sensor coupleable to the walking aid, the second sensor configured to detect an acceleration value and an angular velocity value of the walking aid being used over time; a third sensor coupleable to the walking aid, the third sensor configured to detect a second force applied to the walking aid; a microcontroller electronically coupled to the first sensors, the second sensor, and the third sensor, the microcontroller configured to electronically transmit the first force from the first sensors, the acceleration value and the angular velocity value from the second sensor, and the second force from the third sensor, to a computing device; and a non-transistory computer readable medium having a plurality of instructions executable by an electronic processor of the computing device to analyze a gait pattern of a patient using the walking aid, the gait pattern based on the first force, the acceleration values, the angular velocity values, and the second force.

In yet another embodiment, the invention provides a system for analyzing a state of action of a user of a walking aid. The system comprises a microcontroller configured to receive data from sensors disposed on the walking aid and to transmit the data, the microcontroller configured to communicate with a computing device over a network. The computing device includes an electronic processor having a non-transitory, computer-readable memory storing instructions that, when executed by the processor, cause the computing device to receive the data from the microprocessor supported by the walking aid, convert the data into a frequency domain data set and a time domain data set, evaluate the frequency domain data set and the time domain data set to determine a preferred data set, generate a model defining a set of states of action of the patient based on a set of controlled data, where the controlled data is data collected by the microcontroller during known states of action of the patient, predict the state of action of a patient by comparing the preferred data set of the patient's data to the model, and output the prediction on a display device.

In another embodiment, the invention provides a non-transitory computer readable medium carrying a computer program comprising computer readable instructions configured to cause an electronic processor to carry out a method of analyzing a gait pattern of a patient. The method comprises receiving, as input to the processor, data from sensors on a walking aid; converting, by the processor, the data into a frequency domain data set and a time domain data set; evaluating, by the processor, the frequency domain data set and the time domain data set to determine a preferred data set; generating, by the processor, a model defining a set of states of action of the patient based on a set of controlled data; predicting, by the processor, the state of action of a patient by comparing the preferred data set of the patient's data to the model; and outputting, by the processor, the prediction on a display device.

In a further embodiment, the invention provides a kit for retrofitting an existing walking aid. The kit can comprise an electronics module, such as the electronics module(s) described below. For example, a user can apply sensors (same or different types of sensors) to the walking aid at desired positions on the walking aid or based on manufacturer instructions and couple an electronic processor to the walking aid to collect the data from the sensors. The kit also can comprise a software program executable on a computing device or electronic access to the software program via a network that can process and analyze the data collected by the sensors.

Other aspects of the invention will become apparent by consideration of the detailed description and accompanying drawings.

BRIEF DESCRIPTION OF THE DRAWINGS

FIG. 9A is a schematic view of sensors positioned on a handle of the gait monitoring device illustrated in FIG. 6
FIG. 9B is a cross-sectional view of a bottom portion of the gait monitoring device in FIG. 6.
FIG. 10 is a block diagram of a system for processing data collected by the electronics module illustrated in FIGS. 3 and 7.

DETAILED DESCRIPTION

Figure 1A:
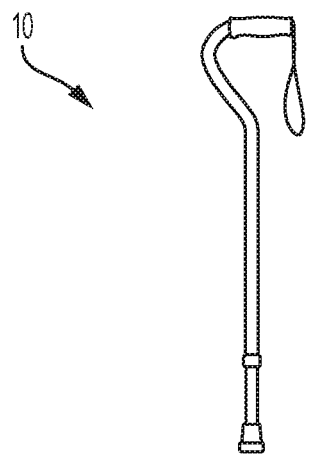
FIG. 1A is a perspective view of a typical walking aid.
Figure 1B:
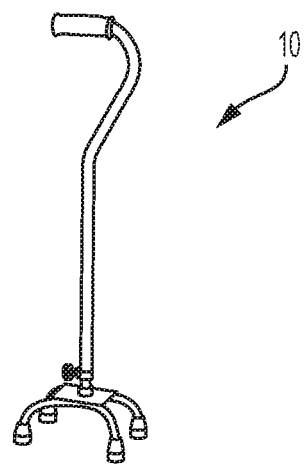
FIG. 1B is a perspective view of a typical walking aid.
Figure 1C:
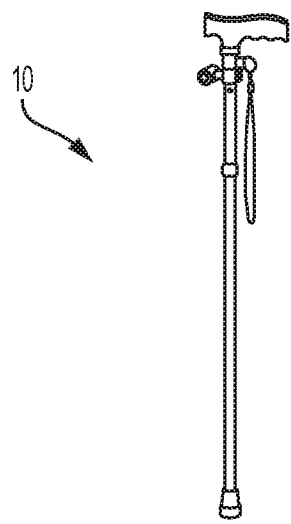
FIG. 1C is a perspective view of a typical walking aid.
Figure 1D:
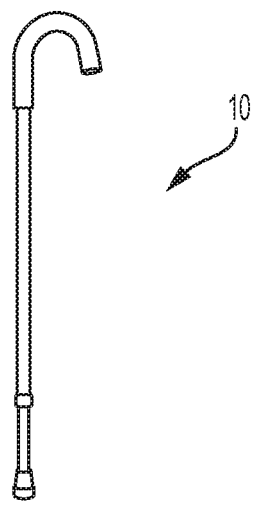
FIG. 1D is a perspective view of a typical walking aid.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, the methods, operations, and sequences described herein can be performed in various orders. Therefore, unless otherwise indicated herein, no required order is to be implied from the order in which elements, steps, or limitations are presented in the detailed description or claims of the present application. Also unless otherwise indicated herein, the method and process steps described herein can be combined into fewer steps or separated into additional steps.

In addition, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc.

It should also be noted that a plurality of hardware and software based devices, as well as a plurality of different structural components may be used to implement embodiments of the invention. In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium) executable by one or more processors. As such, it should be noted that a plurality of hardware and software based devices, as well as a plurality of different structural components may be utilized to implement the invention. For example, "controllers" described in the specification can include one or more electronic processors, one or more non-transitory computer-readable medium modules, one or more input/output interfaces, and various connections (e.g., a system bus) connecting the components.

The design and construction of the electromechanical system involved modifying the mechanical design of a regular cane and instrumenting it with various sensors and microcontroller boards both at the handle and the bottom of the cane. The goal was to be able to modify an off-the-shelf cane such that it can house position, orientation and force sensors, and wireless microcontrollers to collect these data as a person walks without substantially increasing the weight of the cane.

Two key considerations were taken into account for the design of the exterior of the walking aid. The first was to fabricate components to be as modular as possible. This modularity allowed commercially available components to be used in combination with fabricated parts. For example, a user may prefer a quad-base ferrule rather than a basic rubber stop. Another consideration was to make alterations that were as minimally invasive as possible to the appearance of a standard cane. This is due to the trend that individuals issued a walking aid by a healthcare professional will be less likely to use the aid if it is not aesthetically appealing or if it appears too bulky. Additionally, an offset cane was selected for development because it is more commonly used than a straight cane. Note that the ability to adjust the length of the cane to accommodate different users' heights was unaffected by the described modifications.

The design for the handle of the cane replicated the ergonomic form of a typical derby handle used for straight shaft canes. This design conformed to the curve of the hand to provide stability and comfort to the user while still maintaining enough rigid structure to withstand typical loads. Internally, the handle housed the electronic components of the system which will be described in detail below. Multiple embodiments of handles were contemplated to accommodate different arrangements of the electronic components. Each handle was easily interchangeable in order to strengthen the modularity of the system. The housing allowed the internal components to be rigidly mounted which was necessary for reliable inertial measurement from the accelerometer and gyroscope. Additionally, an access port was created in the handle that would allow reprogramming the embedded microcontroller without dismantling the housing.

At the far end of the cane, a modular base connected to the shaft via a spring detent was used to measure axial force and additional inertial information. Because of its modularity, the fabricated base was compatible with several types of commercially available, ¾" diameter walking aid ferrules to adjust to the preferences of the user. A load cell was placed in line with the shaft in order to measure the reaction force exerted by the ground upwards on the cane, which is equal to the force exerted downwards on the cane by the user. This design isolates only the fully axial load while eliminating any torque or shear forces that may be simultaneously applied. The combined mass of the new components in an embodiment of the invention was approximately 100 grams. Considering that typical quad-base ferrules are at least 150 grams suggests that the added components constitute a negligible increase in the cane's mass. In an alternative construction, to reduce the cost and weight, instead of using a load cell, a single force sensing resistor (FSR) could be used in line with the shaft in order to measure the reaction force exerted by the ground upwards on the cane, which is equal to the force exerted downwards on the cane by the user.

FIGS. 1A-D illustrate conventional walking aids 10. Embodiments of the invention described herein are coupled to, attached to, or incorporated within the walking aid 10. As illustrated in FIGS. 1A-D, each walking aid 10 has different features such as size and shape of handle, size and shape of elongated housing, and size and type of base. It is noted that the embodiments of the invention can be utilized with any type of walking aid and that the type, size, or shape of the walking aid are not limiting as to structure or functionality of embodiments of the invention.

Figure 2:
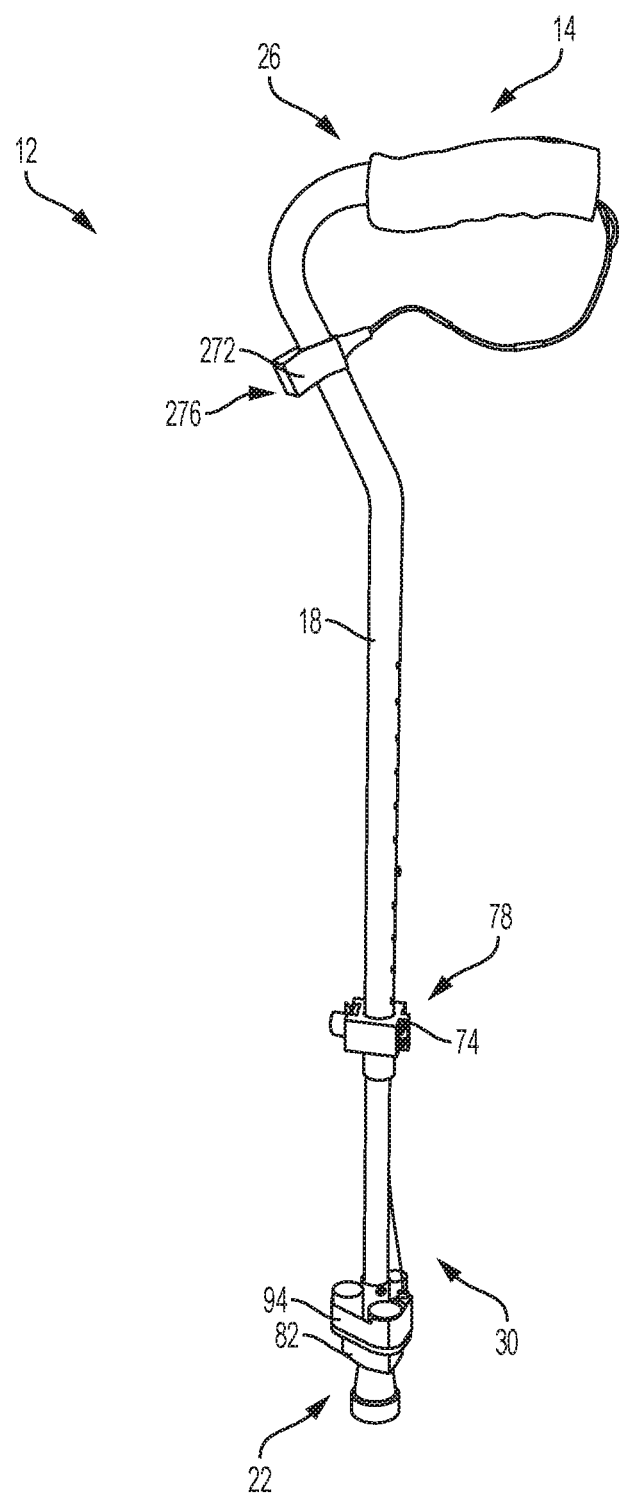
FIG. 2 is a perspective view of a gait monitoring device according to an embodiment of the present invention.

FIG. 2 illustrates a walking aid 12 according to an embodiment of the present invention. The walking aid 12 includes a handle 14 and an elongated housing 18 extending from the handle 14, and a base 22. The elongated housing 18 may comprise a solid material throughout the length or may be hollow along portions of the length or the entire length. The elongated housing 18 may be straight or may incorporate bends or curves. The housing 18 includes a first end 26 coupled to the handle 14 and a second end 30 distal from the handle 14 and coupled to the base 22. The first end 26 of the housing 18 may be integral with the handle 14 in some embodiments. The base 22 is attached or coupled to the second end 30 of the housing 18. The base 22 may take one of several different forms as illustrated in FIGS. 1A-D or other suitable arrangements.

Figure 3:
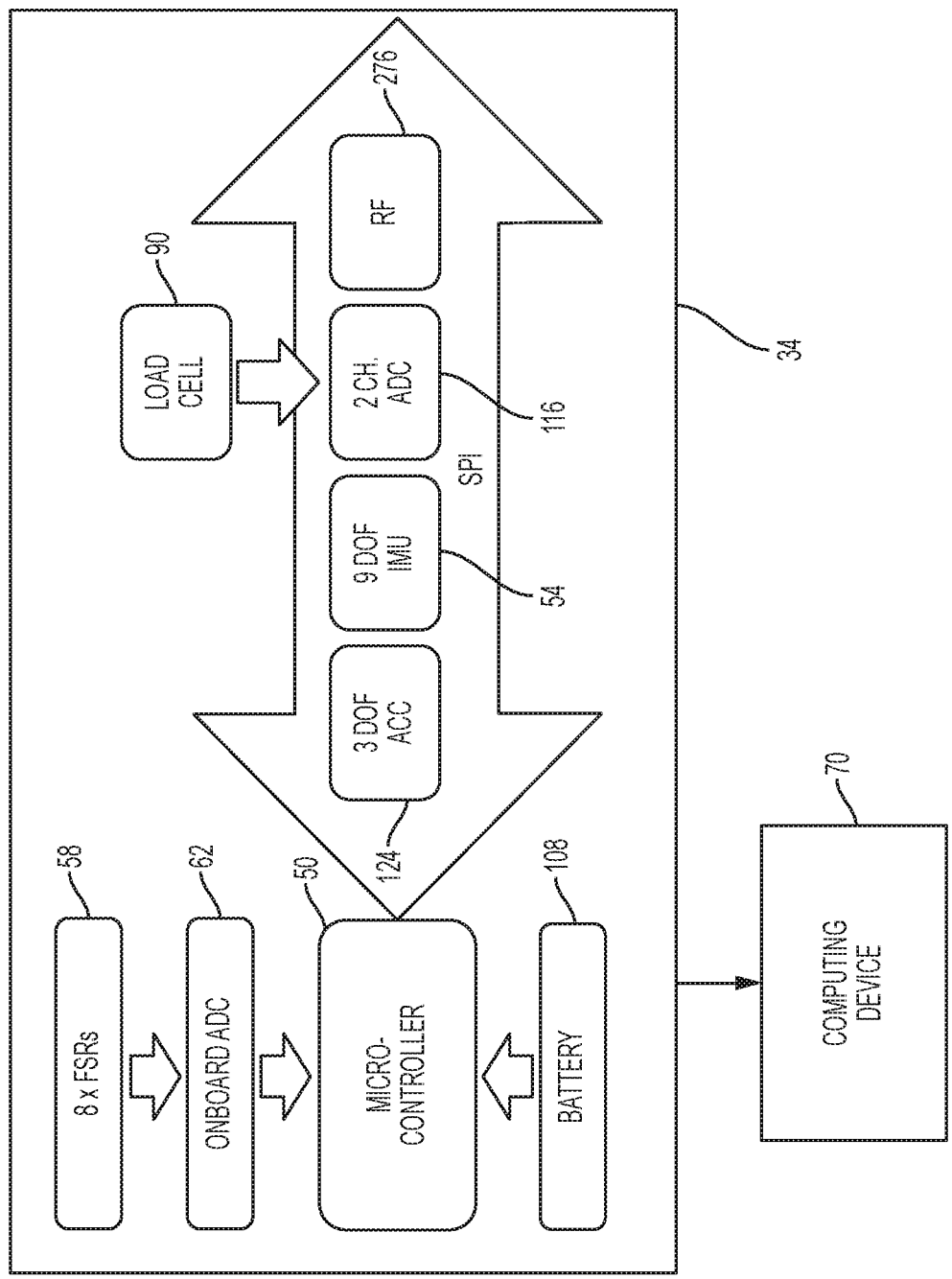
FIG. 3 is a block diagram of an electronics module according to an embodiment of the present invention.
Figure 4A:
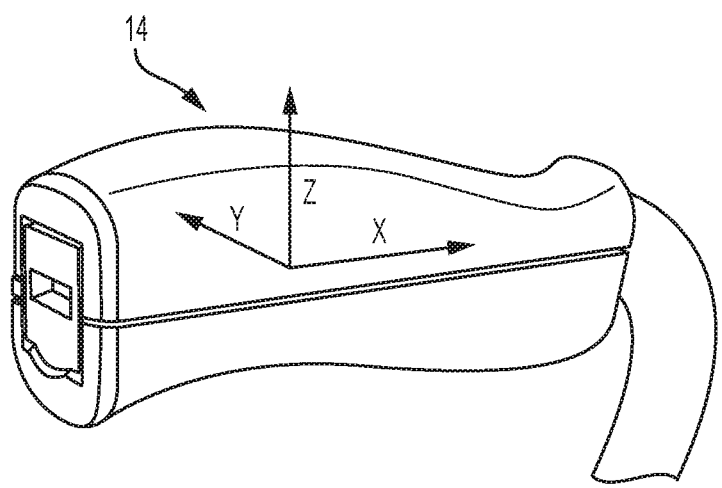
FIGS. 4A-D illustrate perspective views of components of the gait monitoring device illustrated in FIG. 2.
Figure 4B:
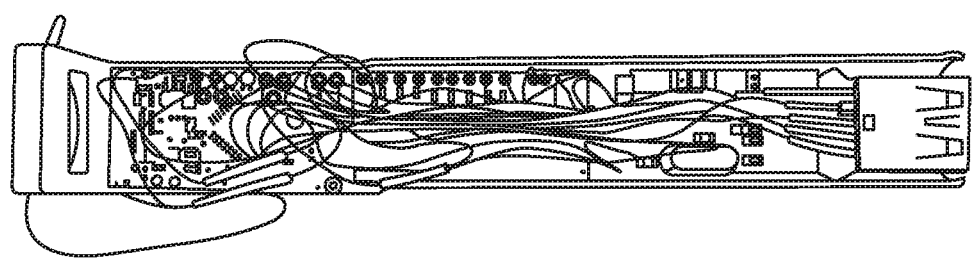

The walking aid 12 includes an electronics module 34 coupled thereto. In this embodiment illustrated in FIGS. 2-4, the electronics module 34 comprises a plurality of electrical components supported by a plurality of housings. The handle 14 houses or supports (see FIGS. 4A and 4B) an electronic processor 50, such as a microcontroller, a first type of sensor 54, a second type of sensor 58, such as force sensing resistors (FSR), and an analog-to-digital converter 62 to receive or acquire force information from the second type of sensors 58, which are positioned on the handle 14. In particular, the first type of sensor 54 is a nine degree of freedom (DOF) inertial measurement unit (IMU). One of the sensors 54 is coupled to the handle 14. The sensor 54 is configured to detect angular velocity and linear acceleration at the handle 14.

Figure 5:
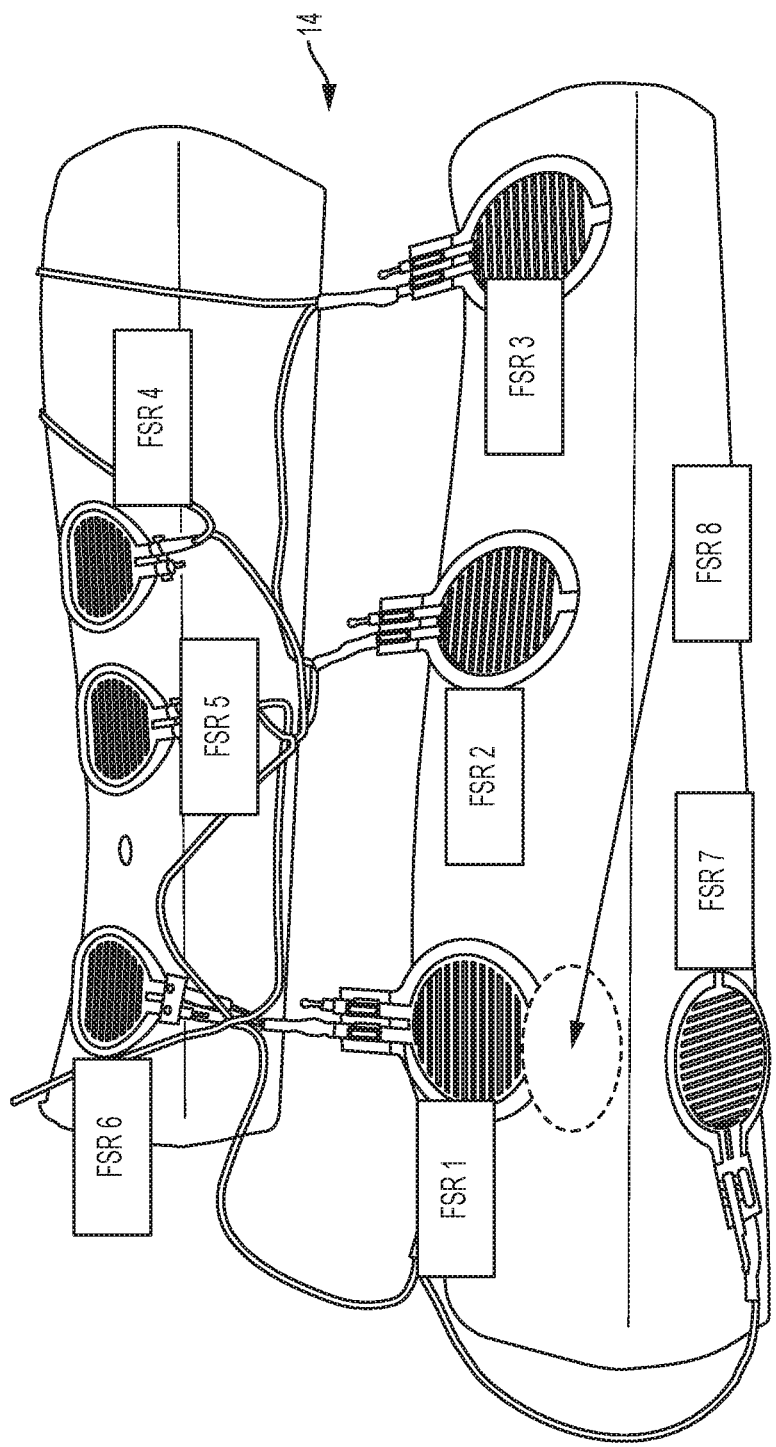
FIG. 5 illustrates a top perspective view of a handle of the gait monitoring device illustrated in FIG. 2.
Figure 6:
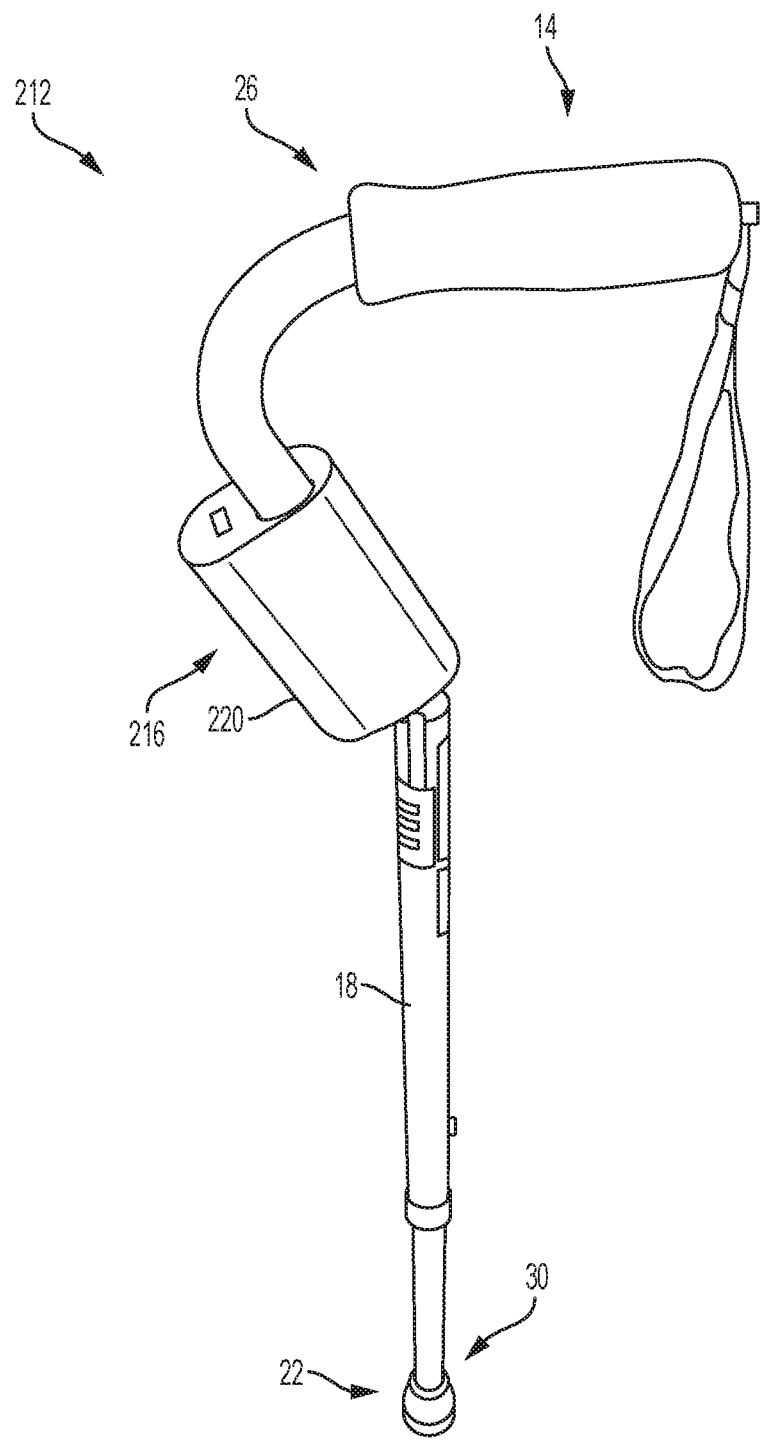
FIG. 6 is a perspective view of a gait monitoring device according to an embodiment of the present invention.

The second type of sensors 58 are configured to detect a force applied to the handle 14. In one embodiment, as illustrated in FIG. 5, eight of the second type of sensors 58 are positioned on the handle 14. A first sensor 58 (FSR 1) is generally positioned on a top surface at a rear portion of the handle 14. A second sensor 58 (FSR 2) is generally positioned on a top surface in a middle portion of the handle 14. A third sensor 58 (FSR 3) is generally positioned on a top surface in a front portion of the handle 14. A fourth sensor 58 (FSR 4) is generally positioned on a bottom surface in the front-middle portion of the handle 14. A fifth sensor 58 (FSR 5) is generally positioned on a bottom surface in a middle portion of the handle 14. A sixth sensor 58 (FSR 6) is generally positioned on a bottom surface in a rear portion of the handle 14. A seventh sensor 58 (FSR 7) is generally positioned on a first side surface between the rear portion and the middle portion of the handle 14. An eighth sensor 58 (FSR 8) is generally positioned on a second side surface opposite the first side surface between the rear portion and the middle portion of the handle 14.

In one embodiment, the analog-to-digital converter 62 can be an eight channel analog to digital converter for converting analog signals detected by the second type of sensors into digital signals. The microcontroller 50 is configured to receive the force information from the second type of sensors 58 and the linear acceleration value and the angular velocity value from the first type of sensor 54. The microcontroller 50 is also configured to transmit the signals to a computing device 70. The transmission may be wireless or via a wired connection.

With further reference to FIG. 2, the walking aid 12 includes a housing 272 coupled to the elongated housing 18. The housing 272 supports a radio frequency circuit 276, which is in electrical communication with the electronic processor 50. The RF circuit 276 communicates with and transmits data from the electronic processor 50 to a remote device such as a dongle (discussed below).

The walking aid 12 also includes a housing 74 coupled to the elongated housing 18. The housing 74 supports a third type of sensor 78, such as an ultrasonic sensor to detect obstacles in a pathway of the walking aid or patient. The third type of sensor 78 is in electrical communication with the electronic processor 50 and periodically emits an ultrasound signal. The electronic processor 50 executes instructions stored thereon to analyze the ultrasound signal to determine the presence of nearby obstacles and can output a signal to the patient of the obstacle. For example, the output signal can be an audible signal (in which case a speaker can be coupled to the walking aid 12) or a vibratory signal (in which case a motor or other device capable of generating a vibration), which can be felt by the patient's hand.

Figure 4C:
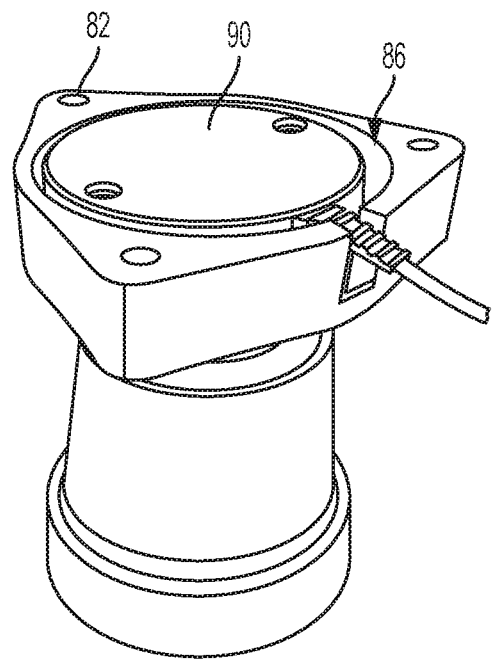
Figure 4D:
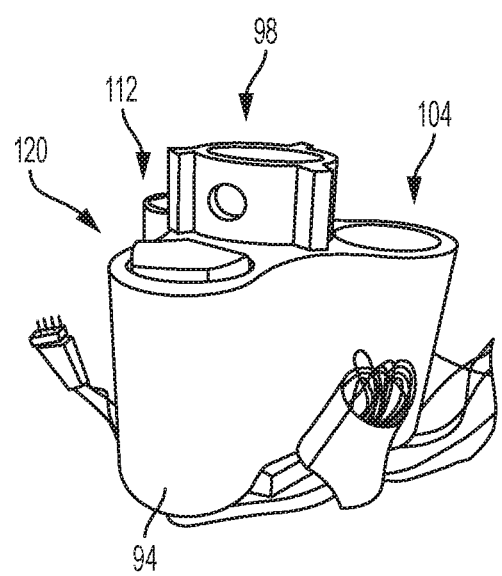

Again, with reference to FIGS. 2 and 4C, the walking aid 12 includes a housing 82 positioned near the base 22. The housing 82 includes a recess 86 that supports a fourth type of sensor 90, such as a load cell, to detect a force applied to the walking aid 12. The housing 82 is coupled to a rubber tip or distal end of the elongated housing 18.

The walking aid 12 also includes a housing 94 coupled to the elongated housing 18. The housing 94 includes a bore 98 for receiving a distal portion of the elongated housing 18. The housing 94 also includes a first recess 104 for receiving a power source 108, a second recess 112 for receiving an analog-to-digital converter 116, such as a two channel ADC, and a third recess 120 for receiving an accelerometer 124. The housing 94 also can be coupled to the housing 82.

FIGS. 6-9B illustrate a walking aid 212 according to another embodiment of the invention. Like the embodiment discussed above, the walking aid 212 includes a handle 14 and an elongated housing 18 extending from the handle 14, and a base 22. The elongated housing 18 may comprise a solid material throughout the length or may be hollow along portions of the length or the entire length. The housing 18 includes a first end 26 coupled to the handle 14 and a second end 30 distal from the handle 14 and coupled to the base 22. The first end 26 of the housing 18 may be integral with the handle 14 in some embodiments. The base 22 is attached or coupled to the second end 30 of the housing 18. The base 22 may take one of several different forms as illustrated in FIGS. 1A-D or other suitable arrangements.

The walking aid 212 includes an electronics module 216 coupled to the exterior of the housing 18 near the handle 14. The base 22 includes an elastic component 36, such as a spring (see FIG. 9B) coupled to the second end 30 of the housing 18. The elastic component 36 can be supported by a housing or container 40, which is coupled to the second end 30 of the housing 18. The elastic component 36 is used to measure axial force and additional inertial information. In this embodiment, the electronics module 216 is coupled to the exterior housing 18 near the handle 14. The electronics module 216 includes a housing 220 for the electronic components (described below). In other embodiments, the electronic components are attached to or coupled to the interior or exterior of the housing 18. The electronic components may or may not be separately or grouped into a separate housing structure.

With reference to FIGS. 6-9B, the electronics module 216 includes a power source 224, such as a battery, a power management unit 228, an electronic processor 232, such as a wireless microcontroller, a first type of sensor 236, and an analog-to-digital converter 240 to receive or acquire force information from a plurality of a second type of sensor 244, such as force sensing resistors (FSR), which are positioned on the handle 14 and the base 22. In particular, the first type of sensor 236 is a nine degree of freedom (DOF) inertial measurement unit (IMU). One of the sensors 236 is coupled to the handle 14, and one of the sensors 236 is coupled to the base 22. The sensors 236 are configured to detect linear acceleration and angular velocity at the handle 14 and the base 22.

The second type of sensors 244 are configured to detect a force applied to the handle 14 and the base 22. In one embodiment, as illustrated in FIGS. 9A-9B, seven of the second type of sensors 244 are positioned on the handle 14 and one of the second type of sensors 244 is positioned at the base 22. A first sensor 244 (FSR 1) is generally positioned on a top surface at a rear portion of the handle 14. A second sensor 244 (FSR 2) is generally positioned on a top surface in a middle portion of the handle 14. A third sensor 244 (FSR 3) is generally positioned on a top surface in a front portion of the handle 14. A fourth sensor 244 (FSR 4) is generally positioned on a bottom surface in a middle portion of the handle 14. A fifth sensor 244 (FSR 5) is generally positioned on a bottom surface in a rear portion of the handle 14. A sixth sensor 244 (FSR 6) is generally positioned on a first side surface between the rear portion and the middle portion of the handle 14. A seventh sensor 244 (FSR 7) is generally positioned on a second side surface opposite the first side surface between the rear portion and the middle portion of the handle 14.

In one embodiment, the analog-to-digital converter 240 can be an eight channel analog to digital converter for converting analog signals detected by the second type of sensors into digital signals. The wireless microcontroller 232 is configured to receive the force information from the second type of sensors 244 and the acceleration value and angular velocity value from the first type of sensors 236. The microcontroller is also configured to transmit the signals to a computing device 248. The transmission may be wireless or via a wired connection.

Example

Figure 7:
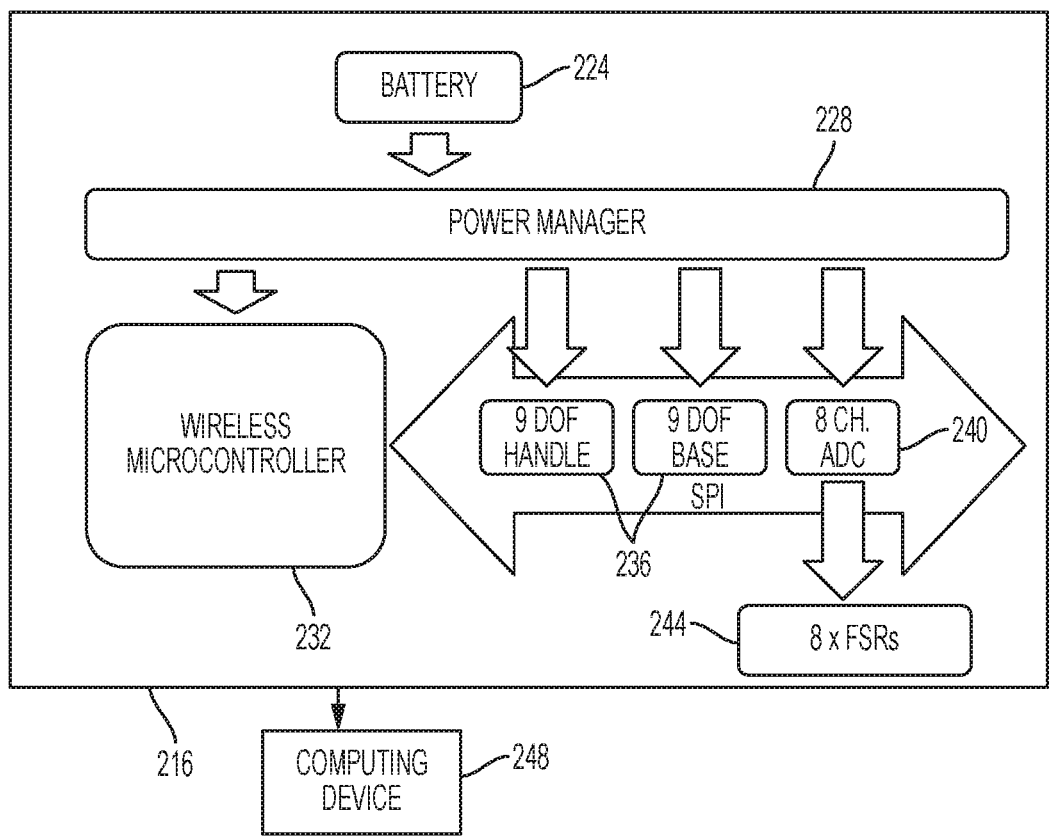
FIG. 7 is a block diagram of an electronics module according to an embodiment of the present invention.
Figure 8:
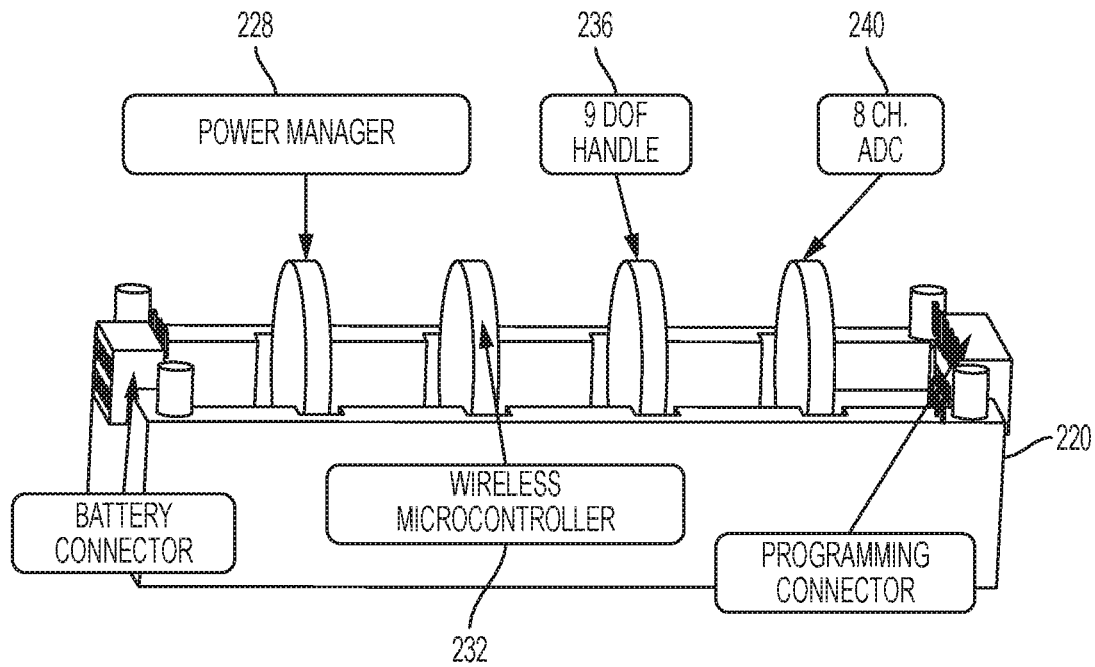
FIG. 8 is a schematic view of components arranged in a housing of the electronics module illustrated in FIG. 7.

One example of the electronics architecture of an embodiment of the invention is illustrated in FIGS. 7-8. This architecture includes six primary modules: a battery, a power management unit, a wireless microcontroller, two separate 9 DOF IMUs located, respectively, in the walking aid handle and in the base, and an eight-channel analog to digital converter to acquire force information from the FSRs. In one embodiment, the instrumentation design used two IMUs to detect linear acceleration and angular velocity at the two extreme endpoints of the walking aid. Two points were chosen because the pattern of acceleration and velocity is different at those positions depending on the current phase of walking. Seven FSRs were used on the handle because that amount provided adequate surface area coverage based on observations of several individuals' handling of the device.

With the exception of the FSRs and the IMU located in the base, the electronic modules were assembled into a plastic, semi-cylindrical housing fabricated by rapid prototyping (OBJET 30, Objet Geometries Ltd, USA). The housing was shaped to easily fit the walking aid handle with a diameter of 14 mm, a height of 14 mm and a length of 35 mm. FIG. 8 shows the arrangement of the embedded components in the housing. Each of the modules includes a separate printed circuit board (PCB) each with a diameter of 9.8 mm and a thickness of 1.6 mm. The modules are connected by soldering wires between their easily accessible pads. The power management unit embeds a low-dropout voltage regulator (TPS73xx, Texas Instrument, USA), and an operational amplifier (ADS8617, Analog Device, USA) to provide a buffered supply to the FSRs independently of the regulator. This module thus generates the 3.3 V needed for all of the modules.

Both the 9 DOF inertial sensors (LSM9DS0, ST Microelectronics, Switzerland) and the eight channel ADC (AD7689, Analog Devices, USA) are controlled by a wireless microcontroller (CC2530, Texas Instrument, USA) through the serial peripheral interface (SPI) at a clock frequency of 1 Mbit/s.

The two inertial sensors were configured to measure accelerations in a range of 4 g, angular velocities of 450 degrees per second (dps) and a magnetic field in a range of 2 gauss (G) with resolutions of 61 µg, 7.5 mdps and 61 µG, respectively. The housing provides a second connector to access the microcontroller pins to easily debug and reprogram the walking aid's main application. The FSRs (FSR 402, Interlink Electronics, USA) were mounted on both the walking aid handle and base as shown in FIGS. 9A and 9B, respectively. All of the FSR output signals were acquired by the 16 bit ADC which results in a resolution of 50.3 µV equal to 0.0015 N. The electronic components of the base module were connected through the body of the walking aid to the handle with 1.2 m wire to allow adjustment of the length of the walking aid.

For the power supply source, two 100 mAh, 3.7 V rechargeable LiPo batteries (Shenzhen Hondark, Electronics Co., Ltd., China, 12 mm×15 mm×3 mm in size) were connected in parallel and used as the onboard power supply source. Connections between the battery power source and the embedded electronics are provided through mating connectors assembled on the battery terminals and on one of the cylinder surfaces, respectively.

As noted above and with reference to FIG. 10, the electronic processor 50, 232 transmits data via radio frequency signals (RF circuitry 276) to a computing device 248 (via a dongle 274, in some embodiments) for further processing and analysis of the data. In other constructions, the electronic processor 50, 232 transmits data via a network 252 to a computing device 248 (with our without a dongle 274) for further processing and analysis of the data. The network 252 may be a wired or a wireless communication network, such as a cellular network (e.g., Long-Term Evolution (LTE)), a local area network (e.g., wireless fidelity (Wi-Fi)), the Internet, a land mobile radio (LMR) network, a Bluetooth™ network, a wireless accessory Personal Area Networks (PAN), a Machine-to-machine (M2M) autonomous network, a public switched telephone network, a future developed network, or any combination or derivative thereof. The computing device 248 may include mobile devices (for example, smartphones, tablets, smart watches, and the like), fixed devices (for example, a desktop computer, a laptop computer, a server, and the like), or a combination thereof. The computing device 248 may include, among other components, a communication interface for communicating over the network 252. The communication interface may include a port or connection for receiving a wired connection to the network 252 (for example, an Ethernet cable, fiber optic cable, a telephone cable, or the like), a wireless transceiver for communicating over the network 252, or a combination thereof.

The computing device 248 can include an electronic processor (e.g., a microprocessor or other programmable device) 256, a memory (e.g., a non-transitory computer-readable medium) 260, an input/output interface 264, and an optional display device 268. The electronic processor 256, the memory 260, and the input/output interface 264 communicate through one or more communication lines or data buses. It should be understood that in other constructions, the computing device includes additional, fewer, or different components. In addition, it should be understood that more than one electronic processor can be used to perform the processing and analysis tasks performed by a single electronic processor. For example, each electronic processor can be programmed to access one or more particular computer-readable media (described below) to execute the instructions stored in the computer-readable media. Each electronic processor can execute a subset of instructions on the computer-readable media and perform a subset of functions that when all discrete functions are taken together, the electronic processors perform and carry out the functions that may be performed by a single electronic processor.

The memory 260 may include a program storage area (e.g., read only memory (ROM)) and a data storage area (e.g., random access memory (RAM), and other non-transitory, machine-readable medium). For example, the data storage area of the memory may store the individual three principal axes components each from linear acceleration, angular rotation and magnetic field orientation and the eight force signals received from the electronic processor 50, 232. The computer-readable medium (e.g., read-only memory, random-access memory, or combinations thereof) stores instructions and data. The electronic processor retrieves instructions from the computer-readable medium and executes the instructions to perform a set of functions including the methods described herein. For example, the computer-readable medium can store a gait analysis application described in more detail below.

Figure 13:
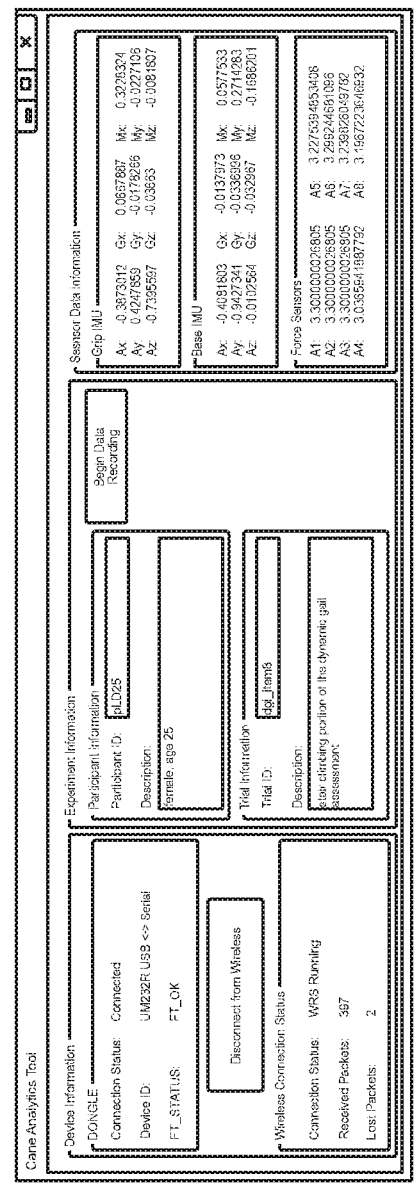
FIG. 13 is a screen capture of a graphical user interface showing data from the gait monitoring device according to an embodiment of the present invention.
Figure 14:
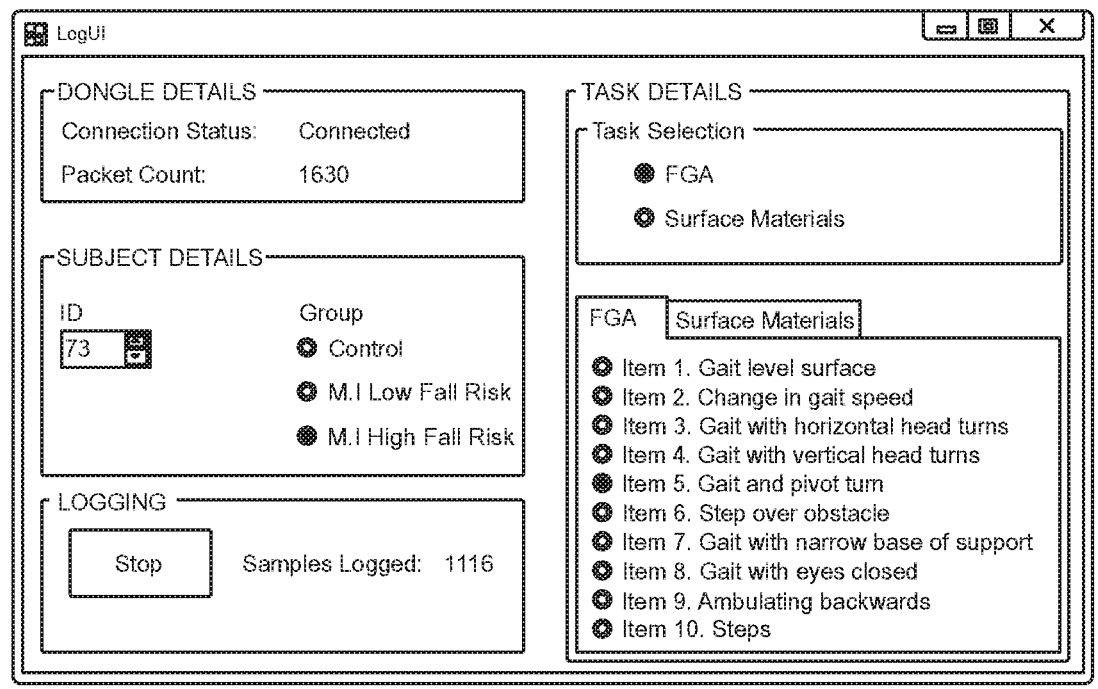
FIG. 14 is a screen capture of a graphical user interface showing data from the gait monitoring device according to an embodiment of the present invention.
Figure 15:
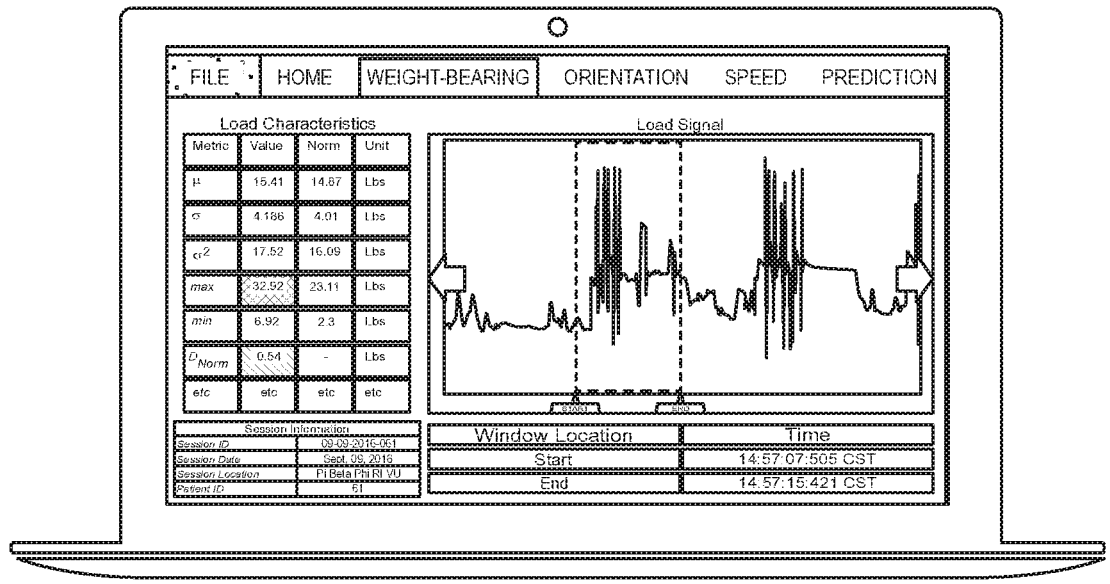
FIG. 15 is a screen capture of a graphical user interface showing data from the gait monitoring device according to an embodiment of the present invention.

The input/output interface 264 allows the computing device 248 to communicate with external devices and systems. The input/output interface 264 receives inputs, provides outputs, or a combination thereof. In some embodiments, the input/output interface 264 receives input from a user through one or more input mechanisms, such as a touch screen, a button, a knob, and the like. Similarly, in some embodiments, the input/output interface 264 provides output to a user through one or more output mechanisms, such as the display device 268. The display device 268 can receive instructions from the electronic processor 256 to present information such as that shown in FIGS. 13-15.

The computing device 248 can communicate with a database or server. The database can store information or data received from the electronic processor 50, 232 and can be accessed to retrieve the information or data for further processing and analysis.

FIG. 10 illustrates a system implementation, the data collection, feature extraction, and predictive analytics. The software component of the system has various modules from sensory interfaces and firmware for data acquisition to signal processing and pattern analysis. Each subcomponent is discussed in more detail in the following Example. FIG. 10 shows the overall system components and their interaction.

Figure 11:
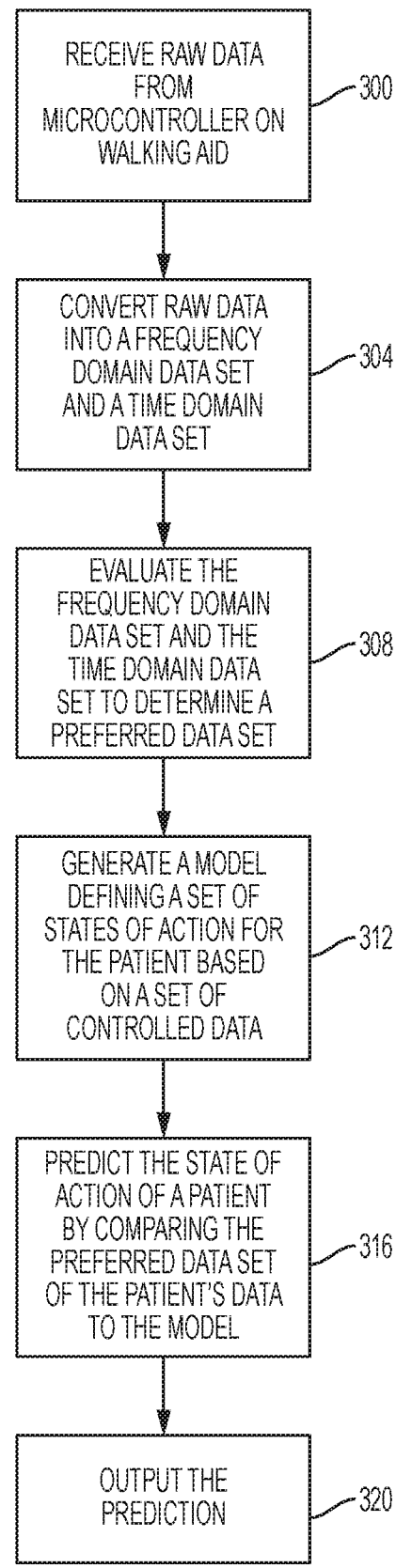
FIG. 11 is a flow chart of a method of analyzing a gait pattern of a patient according to an embodiment of the present invention.

As noted above, the electronic processor 256 of the computing device 248 is configured to retrieve instructions from the computer-readable media and execute, among other things, the instructions to perform control processes and methods to perform a gait analysis of a patient using the walking aid 12. For example, FIG. 11 is a flow chart illustrating a method of analyzing a gait pattern of a patient performed by the electronic processor. The electronic processor 256 receives (at 300) the raw data from the microcontroller 50, 232 and converts (at 304) the data into a frequency domain data set and a time domain data set. The electronic processor 256 evaluates (at 308) the frequency domain data set and the time domain data set to determine a preferred data set and generates (at 312) a model defining a set of states of action of the patient based on a set of controlled data, where the controlled data is data collected by the microcontroller during known states of action of the patient. The electronic processor 256 then predicts (at 316) the state of action of a patient by comparing the preferred data set of the patient's data to the model and outputs (at 320) the prediction to a display device. The output may include additional information to the user via a graphical user interface, such as the screens shown in FIGS. 13-15. A state of action may encompass a position of a patient, e.g., standing, walking, falling, etc.

Example

A. The Embedded System

The data from the sensors 54 and 62 were acquired by the application running on the microcontroller 50 and assembled into a 28 byte sensor payload. The payload was transmitted together with a progressive package indicator, a time stamp, the battery level, RSSI and two synchronization start and stop bytes for a total payload size of 40 bytes. This payload was transmitted by the wireless microcontroller 50 to an external transceiver over a 2.4 GHz carrier frequency. The external transceiver (henceforth referred to as a dongle 274) included a mirror wireless microcontroller (CC2530, Texas Instrument, USA) connected to the USB port of a PC (e.g., computing device 66) through a dedicated module (UM232R, FTDI, UK).

B. Data Acquisition

The data acquisition subsystem was developed to interact with the embedded subsystem on the cane to collect and log the raw and derived data. To keep the cane light, computationally intensive tasks such as logging the raw and derived signals, feature extraction and pattern analytics were offloaded to a remote machine (e.g., computing device 248) via the custom wireless-to-USB dongle 274. The data acquisition subsystem automatically handled connection with the dongle 274 and provided tools for correctly logging time stamped raw and derived sensory data. Moreover, the graphical user interface (FIGS. 13-15, for example) of this system displayed real-time sensory data, session information, as well as packet status information for continuous data monitoring.

C. Raw and Derived Data

A total of 26 raw signals were streamed wirelessly to the dongle 274 and logged by the data acquisition module at approximately 60 Hz. These signals were three principal axes components each from linear acceleration, angular rotation and magnetic field orientation. These 9 degrees of freedom (DOF) signals were collected from both 9 DOF IMUs (3×3×2=18). Moreover, eight force signals were collected from a set of 8 FSRs at the handle and at the bottom of the cane. The sensor data was preprocessed to obtain some derived data. This was applied to twenty of the raw signals (magnetometer data were not included). Techniques for computing the derived data included magnitude of the vectors of acceleration and rotational velocity in all three components as well as components in the transverse plane (i.e., components that are not primarily affected by gravity). The magnitude of a force vector, $F=[f1, f2, \ldots, f8]$, with each component being a reading from a corresponding FSR was also included as part of the overall derived signals and logged together with the raw data for offline feature extraction and gait recognition. The derived signals were found to be quite useful in classifying the associated gait. Table 1 includes a full listing of both raw and derived signals.

D. Feature Extraction and Feature Selection

Various characteristics features were utilized in the literature both in time and frequency domains for accelerometer based activity recognition and fall detection. DC mean and mean of the rectified signal, 25th and 75th percentile medians, standard deviation, and correlations between axes were used as time domain features. Among the frequency domain features investigated in the past included frequency band based Fourier coefficients that are computed using the fast Fourier transform (FFT) or the first K components of the spectral power spectrum, spectral energy, spectral entropy, and discrete cosine transform (DCT) coefficients. It should be noted that a large number of other raw and derived characteristics features exist and may be useful in this application. These features include, but are not limited to, wavelet-related features and discrete cosine-related features. The logged raw and derived signals were processed using a low pass filter with a cut-off frequency of 4 Hz and high pass frequency with 0.33 Hz to remove high frequency noise and DC baseline wander component, respectively. The filtered signals were then sampled using a sliding window of 240 samples (approximately 4 seconds) with 50% overlap.

Time and frequency domain features were computed as the combination was reported in yielding superior classification accuracy. These features are listed categorically as shown in Table 2.

Figure 12:
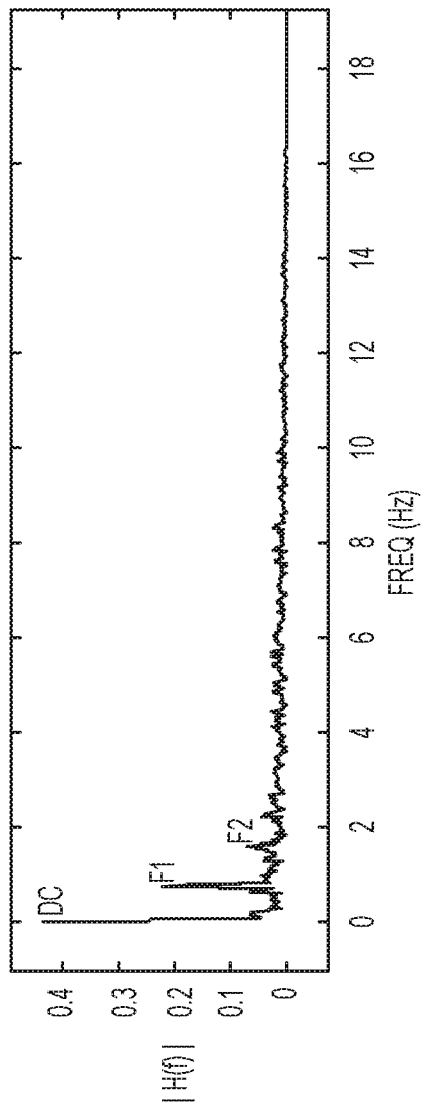
FIG. 12 is a graphical view of sample frequency spectra of a component of acceleration.

The time domain features computed included mean, standard deviation, kurtosis, skewness, correlation coefficients, mean crossing rate, and quantization bins. A 256 sample FFT was computed from the 240-sample sliding window. A Hanning window was used for smooth spectra. The frequency spectra of several subjects were analyzed to determine a suitable range of frequencies to compute the spectral energy. Based on observation most of the useful signal energy seemed to be contained within the range of 0.35 Hz to 1.75 Hz (FIG. 12, Table 3). FIG. 12 illustrates sample frequency spectra of a component of acceleration. For instance, 1.3 Hz±0.1 Hz appeared to be a fundamental frequency of the acceleration signal of the IMU at the handle of the cane.

After the frequency ranges were determined, spectral energy within that range was computed and used as one of the frequency domain feature. The other frequency domain feature used in this study was spectral flux. Spectral flux is defined as a measure of change in magnitude in each frequency range of power spectra and is given by Equation 1. We have modified the equation by taking the L-2 norm as well as dropping the half rectifier function and directly using the first difference.

$$SF(n) = \frac{1}{N}\sum_{k=1}^{N-1}(X[n, k+1] - X[n, k])^2 \qquad (1)$$

Overall, the combination of features gives rise to feature vectors of 818 in length. This feature set is too high dimensional to learn the pattern in a meaningful way. Therefore, a feature selection procedure was performed using a data mining software program WEKA to remove unnecessary features. However, other data mining programs such as KNIME, Rapid Miner, or Apache Mahout, among others, may be used. In this embodiment, features that did not change in 99 percentile rank were removed as non-informative features. Then, a forward greedy hill-climbing search which favors features that are highly correlated with class labels and less correlated with each other was applied and that resulted in only 12 best features based on the evaluation criteria. These final set of features (Table 3) are used for the actual gait recognition. In other embodiments, the feature selection algorithms may include a logistic regression method or a K-Nearest Neighbors method.

E. Methods and Procedure

A system validation study was conducted to collect data for the gait recognition as well as to evaluate the overall system functionality. A total of seven adults with four females (age, M: 27 y SD: 3.9 y) and 3 males (age, M: 27.3 y SD: 4.5 y) completed a range of tasks using the cane for this study. Three different types of tasks were performed to collect useful data from the system. The first task was to walk along a straight, 20 ft. path with the cane. This was done three times for each person. The second task was to complete all eight items of the DGI evaluation. Four participants completed this evaluation which included the following activities: (1) gait on a level surface, (2) change in gait speed, (3) gait with horizontal head turns, (4) gait with vertical head turns, (5) gait and pivot turn, (6) step over obstacles, (7) step around obstacles and (8) stairs. The third task involved simply standing in place while holding the cane at the individual's side. This was done by a single participant for several minutes. Participants were instructed on proper cane usage by a physical therapist and were free to hold the cane in whichever hand they preferred. Data for each task was recorded with information indicating the activity. This information was used to label the data based on the type of activity that it represented (e.g., walking, standing, etc.).

F. Results

Four different classifiers were trained on the data set using WEKA (www.cs.waikato.ac.nz/ml/weka/). These classifiers were C4.5 decision tree, Artificial Neural Network (ANN) with 1 hidden layer (9 nodes), 1 output layer (7 nodes), and an input layer of 12 feature nodes, Support Vector Machine (SVM) with a radial basis function kernel and Naïve Bayes. Table 4 shows a comparison of the prediction accuracies of the four classifiers on each class of the training set as well as the weighted averages. The decision tree C4.5 had the highest performance by far with an overall prediction accuracy of over 95%. ANN had the next best performance with average accuracy of 84%. Although Naïve Bayes and Support Vector Machine (SVM) performed poorly overall, they were each fairly accurate in distinguishing standing and unperturbed walking.

The column titled #Examples in Table 4 lists the total number of examples of each type of example data obtained from a moving four seconds window with 50% overlap. Normal walking and standing were the two largest groups. Note that stairs included both ascending and descending stairs since those tasks were performed sequentially without pause during the DGI evaluation. Tables 5 through 8 show the confusion matrices for all four classifiers evaluated to show the misclassification among classes. Walking had only two misclassified instances and standing was easily distinguished from all other classes with only one example misclassified in Table 5.

These results indicate that the system is able to distinguish many different kinds of walking-related activities based on patterns analyzed using signals from sensors embedded within the device.

Although WEKA was used in the embodiments described, other types of software may be used to analyze the data. Some exemplary alternative software options include, but are not limited to, KNIME, Rapid Miner, and Apache Mahout.

Example

The system is being evaluated with mobility-impaired patients at the Pi Beta Phi Rehabilitation Institute at the Vanderbilt University Medical Center. A preliminary study is underway in which cane usage data is being collected from three distinct groups: controls (non-patients), mobility-impaired patients at high risk for falls, and mobility-impaired patients at low risk for falls. Prior fall risk is decided based on past performance on either the DGI or FGA indices. All subjects completed either the DGI or FGA (depending on past evaluation) during the experimental session. All subjects were 60 years of age or older at the time of the session. This preliminary study has been approved by Vanderbilt University's Institutional Review Board (IRB).

As of this writing, six subjects have completed the experimental session. Thus, only descriptive statistics are presented in Tables 9, 10, and 11. The data shown in these tables are representative of the three major types of sensor data collected (i.e., grip pressure, inertial measurement, and axial force), but these are just a few of many measures that may be obtained with embodiments of the present invention. Moreover, only three of eight distinct activities measured are presented. These are standing in place, normal walking, and stair ascent and descent, shown in Tables 9, 10, and 11, respectively. Tables 9, 10, and 11 reference Equation 2 below.

$$GV(F) = \Sigma_{i=1}^{8} \text{Var}(f_i) \qquad (2)$$

While this data is preliminary in nature, some expected distinctions are immediately apparent. Even with a small sample, the invention is sensitive enough to register clear differences in mean acceleration between different activities (i.e., walking and stair climbing are "faster" activities than idly standing). Objective data obtained from the device is also able to tell us how a person is using it. This can include how much weight the user applies and even whether the user is carrying the cane rather than placing it during normal gait, which is inappropriate and potentially dangerous behavior. Note, for instance, that participant MH12 in Table 10 registers an axial load force of 0 lbf during walking; this suggests that the participant carried the cane while walking. As another example, participant MH11 placed a large amount of weight on the cane while standing; this may be indicative of fatigue or over-reliance on the cane and is the type of information that therapists need, but do not currently have available to them.

Thus, the invention provides, among other things, an instrumented walking cane and a system to predict states of action of a patient based on data from the instrumented cane.

Various features and advantages of the invention are set forth in the following claims.

TABLE 1

Set of raw and derived signals collected from the cane

| | |
|---|---|
| Raw | a1x, a1y, a1z (handle) |
| | a2x, a2y, a2z (base) |
| | g1x, g1y, g1z (handle) |
| | g2x, g2y, g2z (base) |
| | f1, f2, ... ,f8 (all but f6 in handle) |
| derived | $\|\alpha 1\|, \|\alpha 2\|$ |
| | $\|g1\|, \|g2\|$ |
| | $(\|\alpha 1\| + \|\alpha 2\|)^2$ |
| | $(\|g1\| + \|g2\|)^2$ |
| | $\sum \{f1, f2, \ldots, f8\}$ |
| | $\|[f1, f2, \ldots, f8]\|$ |
| | $\|\alpha 1 tran\|, \|\alpha 2 tran\|$ |
| | $\|g1 tran\|, \|g2 tran\|$ |
| | $(\|\alpha 1 tran\| + \|\alpha 2 tran\|)^2$ |
| | $(\|g1 tran\| + \|g2 tran\|)^2$ |

TABLE 2

Category of features extracted from raw/derived data.

| | |
|---|---|
| Time Domain | Mean |
| | Standard Deviation |
| | Skewness |
| | Kurtosis |
| | Quantization Bins (10 bins) |
| | Correlation Coefficient |
| | Mean Crossing Rate |
| Frequency Domain | Spectral energy |
| | Spectral flux |

TABLE 3

The 12 best features after feature selection.

| Domain | Feature | Raw/Derived Signal |
|---|---|---|
| Frequency | Spectral Energy | a1z (1 Hz ± 0.1 Hz) |
| | | a1z (1.3 Hz ± 0.1 Hz) |
| | | a2y (1.15 Hz ± 0.1 Hz) |
| | | g2x (1.75 Hz ± 0.75 Hz) |
| | | ‖F‖ (0.8 Hz ± 0.1 Hz) |
| | Spectral Flux | a1x |
| | | g1x |
| | | ‖F‖ |
| | | ‖a2tran‖ |
| Time | Mean | f3 |
| | Standard Deviation | $(\|a1\|+\|a2\|)^2$ |
| | Quantization Bins | ‖g2‖ |

TABLE 4

Performance Accuracies of Four Classifiers on Training Data

| Class | # Examples | C4.5 | ANN | SVM | Naïve Bayes |
|---|---|---|---|---|---|
| Walking | 147 | 98.6% | 96.6% | 71.4% | 76.9% |
| Eyes Closed | 37 | 94.6% | 67.6% | 18.9% | 73.0% |
| Stairs | 27 | 88.9% | 74.1% | 33.3% | 40.7% |
| Look to Sides | 14 | 85.7% | 42.9% | 28.6% | 35.7% |
| Look Up/Down | 17 | 88.2% | 64.7% | 47.1% | 70.6% |
| Standing | 89 | 98.9% | 97.8% | 92.1% | 98.9% |
| Avoid Obstacles | 51 | 92.2% | 58.8% | 60.8% | 15.7% |
| Overall | 382 | 95.8% | 84.0% | 64.4% | 69.1% |

TABLE 5

Confusion Matrix for C4.5 DT

| | Walking | Eyes Closed | Stairs | Look to Sides | Look Up/Down | Standing | Avoid Obstacles |
|---|---|---|---|---|---|---|---|
| Walking | 98.6% | 0.7% | 0.0% | 0.0% | 0.0% | 0.0% | 0.7% |
| Eyes Closed | 2.7% | 94.6% | 0.0% | 0.0% | 0.0% | 0.0% | 2.7% |
| Stairs | 0.0% | 0.0% | 88.9% | 0.0% | 3.7% | 0.0% | 7.4% |
| Look to Sides | 7.1% | 0.0% | 0.0% | 85.7% | 0.0% | 0.0% | 7.1% |
| Look Up/Down | 0.0% | 5.9% | 5.9% | 0.0% | 88.2% | 0.0% | 0.0% |
| Standing | 0.0% | 0.0% | 1.1% | 0.0% | 0.0% | 98.9% | 0.0% |
| Avoid Obstacles | 5.3% | 0.0% | 2.0% | 0.0% | 0.0% | 0.0% | 92.2% |

TABLE 6

Confusion Matrix for SVM

| | Walking | Eyes Closed | Stairs | Look to Sides | Look Up/Down | Standing | Avoid Obstacles |
|---|---|---|---|---|---|---|---|
| Walking | 71.4% | 0.0% | 0.7% | 0.0% | 0.0% | 25.2% | 2.7% |
| Eyes Closed | 48.6% | 18.9% | 2.7% | 0.0% | 0.0% | 2.7% | 27.0% |
| Stairs | 25.9% | 11.1% | 33.3% | 0.0% | 0.0% | 0.0% | 29.6% |
| Look to Sides | 50.0% | 0.0% | 0.0% | 28.6% | 7.1% | 0.0% | 14.3% |
| Look Up/Down | 17.6% | 0.0% | 0.0% | 5.9% | 47.1% | 0.0% | 29.4% |
| Standing | 6.7% | 0.0% | 0.0% | 0.0% | 0.0% | 92.1% | 1.1% |
| Avoid Obstacles | 33.3% | 0.0% | 0.0% | 0.0% | 0.0% | 5.9% | 60.8% |

TABLE 7

Confusion Matrix for ANN

| | Walking | Eyes Closed | Stairs | Look to Sides | Look Up/Down | Standing | Avoid Obstacles |
|---|---|---|---|---|---|---|---|
| Walking | 96.6% | 2.7% | 0.0% | 0.0% | 0.0% | 0.7% | 0.0% |
| Eyes Closed | 13.5% | 67.6% | 0.0% | 0.0% | 0.0% | 2.7% | 16.2% |
| Stairs | 0.0% | 3.7% | 74.1% | 3.7% | 0.0% | 7.4% | 11.1% |
| Look to Sides | 7.1% | 14.3% | 0.0% | 42.9% | 0.0% | 0.0% | 35.7% |

TABLE 7-continued

Confusion Matrix for ANN

| | Walking | Eyes Closed | Stairs | Look to Sides | Look Up/ Down | Standing | Avoid Obstacles |
|---|---|---|---|---|---|---|---|
| Look Up/ Down | 0.0% | 23.5% | 5.9% | 0.0% | 64.7% | 0.0% | 5.9% |
| Standing | 0.0% | 2.2% | 0.0% | 0.0% | 0.0% | 97.8% | 0.0% |
| Avoid Obstacles | 11.8% | 17.6% | 0.0% | 9.8% | 0.0% | 2.0% | 58.8% |

TABLE 8

Confusion Matrix for Naïve Bayes

| | Walking | Eyes Closed | Stairs | Look to Sides | Look Up/ Down | Standing | Avoid Obstacles |
|---|---|---|---|---|---|---|---|
| Walking | 76.9% | 13.6% | 3.4% | 2.0% | 0.0% | 0.0% | 4.1% |
| Eyes Closed | 21.6% | 73.0% | 0.0% | 2.7% | 0.0% | 0.0% | 2.7% |
| Stairs | 18.5% | 29.6% | 40.7% | 3.7% | 3.7% | 0.0% | 3.7% |
| Look to Sides | 42.9% | 7.1% | 0.0% | 35.7% | 0.0% | 0.0% | 14.3% |
| Look Up/ Down | 5.9% | 11.8% | 0.0% | 5.9% | 70.6% | 0.0% | 5.9% |
| Standing | 0.0% | 1.1% | 0.0% | 0.0% | 0.0% | 98.9% | 0.0% |
| Avoid Obstacles | 21.6% | 43.1% | 3.9% | 3.9% | 11.8% | 0.0% | 15.7% |

TABLE 9.

Preliminary Patient Data - Standing in Place

| | | Subject ID | | | | | |
|---|---|---|---|---|---|---|---|
| Signal (unit) | Metric | C10 | MH10 | MH11 | MH12 | ML10 | ML11 |
| Transverse Plane Acceleration Handle (g) | M ± SD | 0.087 ± 0.012 | 0.087 ± 0.011 | 0.103 ± 0.053 | 0.082 ± 0.029 | 0.097 ± 0.032 | 0.189 ± 0.027 |
| | Peak | 0.132 | 0.109 | 0.271 | 0.173 | 0.244 | 0.248 |
| Handle Grip (lb$^2$) | Volatility | 1.121 | 0.131 | 226.291 | 1.175 | 17.363 | 0.234 |
| Load (lbf) | Peak | NA | 0 | 8.837 | 0 | NA | 0 |

Note: Subject identifiers are assigned based on group affiliation and numerical order, where "C" indicates "control," "ML" indicates "mobility-impared low falls risk," and "MH" indicates "mobility-impared high falls risk."
Handle grip volatility computed as the sum of the variances for each of the eight force-sensing resistor (FSR)-inputs (see Eq. 2)
NA: Load data not collected for these subjects due to modification to sensor unit.

TABLE 10

Preliminary Patient Data - Walking

| | | Subject ID | | | | | |
|---|---|---|---|---|---|---|---|
| Signal (unit) | Metric | C10 | MH10 | MH11 | MH12 | ML10 | ML11 |
| Transverse Plane Acceleration Handle (g) | M ± SD | 0.286 ± 0.326 | 0.223 ± 0.244 | 0.218 ± 0.106 | 0.26 ± 0.159 | 0.215 ± 0.268 | 0.218 ± 0.153 |
| | Peak | 3.255 | 2.614 | 0.666 | 0.913 | 2.597 | 1.137 |
| Handle Grip (lb$^2$) | Volatility | 50.305 | 62.481 | 162.616 | 7.879 | 121.475 | 7.416 |
| Load (lbf) | Peak | NA | 6.817 | 8.337 | 0 | NA | 1.443 |

Note: Subject identifiers are assigned based on group affiliation and numerical order, where "C" indicates "control," "ML" indicates "mobility-impared low falls risk," and "MH" indicates "mobility-impared high falls risk."
Handle grip volatility computed as the sum of the variances for each of the eight force-sensing resistor (FSR)-inputs (see Eq. 2)
NA: Load data not collected for these subjects due to modification to sensor unit.

TABLE 11

Preliminary Patient Data - Stairs

| | | Subject ID | | | | | |
|---|---|---|---|---|---|---|---|
| Signal (unit) | Metric | C10 | MH10 | MH11 | MH12 | ML10 | ML11 |
| Transverse Plane Acceleration Handle (g) | M ± SD | * | 0.187 ± 0.134 | ** | 0.199 ± 0.162 | 0.139 ± 0.1 | 0.21 ± 0.143 |
| | Peak | * | 1.503 | ** | 1.729 | 1.437 | 1.357 |

TABLE 11-continued

Preliminary Patient Data - Stairs

| Signal (unit) | Metric | C10 | MH10 | MH11 | MH12 | ML10 | ML11 |
|---|---|---|---|---|---|---|---|
| Handle Grip (lb$^2$) | Volatility | * | 37.495 | ** | 16.464 | 67.875 | 42.625 |
| Load (lbf) | Peak | * | 2.002 | ** | 3.65 | NA | 7.836 |

Note: Subject identifiers are assigned based on group affiliation and numerical order, where "C" indicates "control," "ML" indicates "mobility-impared low falls risk," and "MH" indicates "mobility-impaired high falls risk."
Handle grip volatility computed as the sum of the variances for each of the eight force-sensing resistor (FSR)-inputs (see Eq. 2)
NA: Load data not collected for these subjects due to modification to sensor unit.
*: Data not recorded due to human error.
**: Cane not used by subject for stairs based on instruction of Physical Therapist.

What is claimed is:

1. A gait monitoring system for determining a state of action of a patient, the system comprising:
    a walking aid including:
        an elongated housing having a first end and a second end;
        a handle coupled to the first end of the elongated housing;
        a base coupled to the second end of the elongated housing distal from the handle, wherein the base is configured to bear weight applied to the handle; and
        a power source coupled to the elongated housing;
    a plurality of first sensors disposed on the handle, each of the first sensors configured to detect a first force applied to the handle;
    a second sensor unit coupled to the handle and configured to detect an acceleration value and an angular velocity value at the handle;
    a third sensor coupled to the base and configured to detect a second force applied to the base;
    a fourth sensor unit coupled to the base and configured to detect an acceleration value and an angular velocity value at the base, wherein the second sensor unit and the fourth sensor unit are positioned at two different points on the walking aid such that different patterns of acceleration and velocity are detected at the two different points depending on a phase of walking; and
    a microcontroller in electrical communication with the first sensors, the second sensor unit, the third sensor, and the fourth sensor unit, the microcontroller configured to electronically transmit the first forces from the first sensors, the acceleration value and the angular velocity value from the second sensor unit, the second force from the third sensor, and the acceleration value and the angular velocity value from the fourth sensor unit to a computing device for electronic processing and outputting of information related to a gait pattern of a patient, the computing device including
        a memory configured to store instructions associated with a gait pattern prediction application;
        one or more processors coupled to the memory, the one or more processors executing the gait pattern prediction application in conjunction with the instructions stored in the memory, wherein the one or more processors are configured to:
            receive data from the plurality of first sensors, the second sensor unit, the third sensor, and the fourth sensor unit;
            preprocess the data from the plurality of first sensors, the second sensor unit, the third sensor, and the fourth sensor unit to obtain derived data;
            apply a sliding window technique to segment the derived data into fixed length intervals;
            convert the data from the plurality of first sensors, the second sensor unit, the third sensor, and the fourth sensor unit into a frequency domain data set and a time domain data set using feature extraction techniques;
            extract features of the time domain data set and from the frequency domain data set;
            apply a feature selection technique to the extracted features to rank the extracted features;
            determine a preferred data set from the extracted features in the time domain data set and the frequency domain data set that are representative of a state of action of the patient;
            generate a model defining a set of states of action of the patient, the model based on a set of controlled walking aid data; and
            predict the state of action of the patient by comparing the preferred data set of the patient's walking aid data to the model based on the controlled walking aid data; and
            output the prediction on a display device.

2. The gait monitoring system of claim 1, wherein the microcontroller is positioned with the elongated housing or the handle or the base.

3. The gait monitoring system of claim 1, further comprising a housing coupled to the elongated housing or the base, the housing defining a first recess configured to receive the third sensor.

4. The gait monitoring system of claim 3, wherein the third sensor is a load cell.

5. The gait monitoring system of claim 1, further comprising a housing coupled to the elongated housing, the housing configured to support a power source, an analog-to-digital converter, and an accelerometer.

6. The gait monitoring system of claim 5, wherein the housing includes a first recess configured to receive the power source, a second recess configured to receive the analog-to-digital converter, and a third recess configured to receive the accelerometer.

7. The gait monitoring system of claim 1, further comprising an analog to digital converter (ADC) in electronic communication with the microcontroller, the ADC configured to receive the first force data from the first sensors.

8. The gait monitoring system of claim 1, wherein at least eight of the first sensors are positioned on the handle of the walking aid.

9. The gait monitoring system of claim 1, wherein the states of action are standing in place, walking, stair ascent, or stair descent.

10. A non-transitory computer readable medium carrying a computer program comprising computer readable instructions configured to cause an electronic processor to carry out a method of determining a state of action of a patient, the method comprising:
- receiving, as input to the processor, data from a plurality of force sensors distributed on a walking cane and a plurality of inertial sensors distributed on the walking cane, wherein the walking cane is able to bear weight and the patient is a user of the walking cane;
- preprocessing the data from the force sensors and the inertial sensors to obtain derived data;
- apply a sliding window technique to segment the derived data into fixed length intervals;
- converting, by the processor, the data from the force sensors and the inertial sensors into a frequency domain data set and a time domain data set using feature extraction techniques;
- extracting features of the time domain data set and from the frequency domain data set;
- applying a feature selection technique to the extracted features to rank the extracted features;
- extracting selected features in the sliding window of the time domain data set and from the frequency domain data set;
- determining, by the processor, a preferred data set from the extracted features in the time domain data set and the frequency domain data set that are representative of a state of action of the patient;
- generating, by the processor, a model defining a set of states of action of the patient, the model based on a set of controlled walking cane data; and
- predicting, by the processor, the state of action of the patient by comparing the preferred data set of the patient's walking cane data to the model based on the controlled walking cane data; and
- outputting, by the processor, the prediction on a display device in a graphical user interface of a clinical tool for gait analysis, gait device prescription, or gait training.

11. The non-transitory computer readable medium of claim 10, wherein the controlled walking cane data is data collected by a microcontroller coupled to the walking cane during known states of action of the patient.

12. The non-transitory computer readable medium of claim 10, wherein the states of action are standing in place, walking, stair ascent, or stair descent.

* * * * *